United States Patent [19]

Cordon et al.

[11] 4,144,322
[45] Mar. 13, 1979

[54] REDUCTION OF ABRASIVENESS IN DENTRIFICES

[75] Inventors: Martin Cordon, Highland; Robert E. Dickson, Belle Mead, both of N.J.

[73] Assignee: Colgate Palmolive Company, New York, N.Y.

[21] Appl. No.: 754,464

[22] Filed: Dec. 27, 1976

Related U.S. Application Data

[63] Continuation-in-part of Ser. No. 544,618, Jan. 28, 1975, abandoned.

[51] Int. Cl.$^2$ .............................................. A61K 7/16
[52] U.S. Cl. ......................................................... 424/49
[58] Field of Search ................................... 424/49–58

[56] References Cited

U.S. PATENT DOCUMENTS

| | | | |
|---|---|---|---|
| 1,817,664 | 8/1931 | Badanes | 424/49 |
| 1,968,858 | 8/1934 | Sheffield et al. | 424/49 |
| 2,010,910 | 8/1935 | Atkins | 424/49 |
| 2,059,396 | 11/1936 | Ripert | 424/49 |
| 3,060,098 | 10/1962 | Gershon | 424/49 |
| 3,689,636 | 9/1972 | Svajda | 424/49 |
| 3,863,006 | 1/1975 | Hodosh | 424/49 |
| 3,943,240 | 3/1976 | Delaney | 424/49 |
| 3,946,108 | 3/1976 | Tomlinson et al. | 424/49 |
| 3,957,968 | 5/1976 | Cordon | 424/57 |
| 4,038,380 | 7/1977 | Cordon | 424/49 |
| 4,060,599 | 11/1977 | Cordon | 424/49 |

*Primary Examiner*—Shep K. Rose
*Attorney, Agent, or Firm*—Robert L. Stone; Murray M. Grill; Herbert S. Sylvester

[57] ABSTRACT

Dentrifice possessing superior cleaning and polishing characteristics comprising a silicious and calcined alumina abrasive system in an amount to provide an enamel abrasion to the dentrifice of above about 450, (as measured by radioactive method) about 0.1–5% by weight and preferably 1–5% of a calcium, magnesium or sodium salt selected from the group consisting of the carbonates, bicarbonates, chlorides, phosphates, silicates and nitrates, with or without raising the pH of said composition to preferably above about 7, so as to reduce said enamel abrasion thereof.

9 Claims, No Drawings

REDUCTION OF ABRASIVENESS IN DENTRIFICES

This application is a continuation in part of copending patent application Ser. No. 544,618, filed January 28, 1975, now abandoned.

This invention relates to a dentifrice having superior cleaning and polishing characteristics containing a relatively abrasive oral cleaning agent, i.e. a hydrated silicious abrasive and a calcined alumina abrasive having a particle size of about 1-15 microns in diameter, in an amount to provide a radioactive enamel abrasion value (REA) above about 450 to the dentifrice; said calcined alumina being preferably present in an amount of at least about 7.5% and said silicious abrasive being present in amounts of at least 10% by weight of said dentifrice; and small amounts of a calcium, magnesium or sodium salt, to reduce the enamel abrasion of said composition, which may be further reduced by raising the pH of said dentifrice.

It has been difficult heretofore to provide dentifrices for use in the daily brushing and cleaning of teeth which provide a desirable balance of cleaning and polishing actions. This has been largely due to the difficulty in selecting suitable abrasives which will afford maximum removal of difficult stains and debris without damaging the enamel surfaces of the teeth.

The function of an abrasive substance in formulations inntended for use in the oral cavity is to remove various deposits, including pellicle film from the surface of the teeth. Pellicle film is a tightly adherent film which often contains brown or yellow pigments and imparts an unsightly appearance to the teeth. An advantageous abrasive material for incorporation into dental formulations should maximize film removal without causing undue abrasion to the hard tooth tissues. The typical soft abrasive used in dental compositions, such as dicalcium phosphate and calcium pyrophosphate, although not unduly abrasive to tooth tissue, are not as effective as the hard abrasives in removing these undesirable deposits from the teeth. However, hard abrasives can present serious problems when present in dental preparations since their outstanding abrasive characteristics are likely to cause undue abrasion to the oral hard tissues (enamel, dentin and cementum).

It has now been found that the addition of about 0.1-5% and preferably 1-5% by weight of a calcium, magnesium or sodium salt to a dental abrasive system comprising hydrated silicious abrasive and the hard abrasive calcined alumina, with or without raising the pH of said dentifrice above about 7, effects a substantial reduction in the radioactive enamel abrasion thereof. This is a particularly desirable feature when applied to an abrasive system containing the hard abrasive calcined alumina. Dentifrice formulations can now be made containing hard abrasives (heretofore relatively undesirable because of their tendency to abrade tooth enamel) to give superior polishing and cleaning without encountering the problem of excess enamel abrasion. In addition to reduced REA (radioactive enamel abrasion) values, there were other beneficial changes observed on highly polished human enamel surfaces brushed with these dentifrices; namely, less grooving or scratching was seen under the microscope.

Accordingly, a dentifrice possessing superior cleaning and polishing action without increasing the enamel abrasivity thereof can be formulated comprising small amounts of a calcium, magnesium or sodium compound, an abrasive system consisting of hydrated silicious abrasive and calcined alumina having a particle size of about 1 to 15 microns in diameter and in an amount to provide a radioactive enamel abrasion value (REA) above about 450.

It has also been found that the enamel abrasion, as evidenced by REA values, is also reduced by increasing the pH of a dentifrice as shown in the following table, wherein the pH of a composition comprising 24% silicious abrasive and 10% alumina abrasive was modified by the addition of HCl and NaOH.

TABLE 1

| pH | additive | REA | RDA* |
|---|---|---|---|
| 4 | HCl | 4855 | 714 |
| 5 | HCl | 2563 | 432 |
| 6 | HCl | 1200 | 338 |
| 6.6 | unadjusted | 891 | 353 |
| 7 | NaOH | 792 | 342 |
| 8 | NaOH | 656 | 348 |
| 9 | NaOH | 488 | 349 |
| 10 | NaOH | 434 | 346 |

*Radioactive Dentin Abrasion Value

This table clearly shows that the enamel abrasivity is sensitive to pH in the 5-10 range with the abrasivity decreasing as the pH increases; whereas the dentin abrasivity remains substantially the same within the pH range of 6-10.

The effectiveness of reducing the enamel abrasivity by modifying the pH of a dentifrice containing a silicious abrasive and calcined alumina with and without 5% $CaCl_2$ is clearly shown in the following table wherein the abrasive constituted 10% alumina and 24% silicious abrasive.

TABLE II

| | REA | | RDA | |
|---|---|---|---|---|
| pH | none | 5% $CaCl_2$ | none | 5% $CaCl_2$ |
| 5 | 1374 | 723 | 458 | 392 |
| 7 | 858 | 461 | 416 | 411 |
| 9 | 663 | 436 | 442 | 424 |

This table also shows the combined salt and pH effects on enamel abrasivity. It is noted that the dentin abrasivity remains substantially unaffected.

The following table additionally shows the additive or combined effects of pH and the salt additive on the enamel abrasivity of a dentifrice comprising 24% hydrated silicious abrasive and 10% calcined alumina, using 5% salt. The pH of the dental creams were unadjusted.

TABLE III

| | REA | | | RDA | | |
|---|---|---|---|---|---|---|
| Salt | Test 1 | Test 2 | Test 3 | Test 1 | Test 2 | pH |
| None (Control) | 859 | 783 | 704 | 323 | 324 | 6.2 |
| $CaCO_3$ | 284 | | | 377 | | 7.9 |
| $CaHPO_4 . 2H_2O$ | 316 | | | | 291 | 6.9 |
| $CaHPO_4$ anhy. | | 574 | | | 383 | 6.6 |
| $CaSiO_3$ | | | 234 | — | — | 7.8 |
| $CaCl_2$ | | 406 | | | 271 | 5.9 |
| $Ca(NO_3)_2$ | 589 | | | 267 | | 5.7 |
| $Mg-SiO_4$ | | | 288 | — | — | 8.1 |
| $MgCO_3 .$ $Mg(OH)_2$ | | 282 | | | 340 | 8.9 |
| $MgCl_2$ | | 648 | | | 325 | 5.7 |
| $NaHCO_3$ | | 342 | | | 309 | 8.3 |
| NaOH to adjust pH | | | 431 | — | —8.2 | |

Accordingly, it is preferable to adjust the pH of the dentifrice so as to obtain a further reduction in the enamel abrasivity thereof. This may be effected by the addition of suitable alkaline buffering agents or by the very presence of the calcium, magnesium, or sodium salts heretofore described. pH adjustment can be obtained by the addition of appropriate amounts of sodium hydroxide, sodium hydrogen phosphate, trisodium phosphate, sodium bicarbonate, etc. Particularly useful buffer systems include sodium carbonate-bicarbonate; tetrasodium pyrophosphate; and a phosphate buffer system comprising $Na_2HPO_4$ and $Na_3PO_4$; wherein there is selected the appropriate ratio of compounds to give the desired pH.

The group of salts found particularly effective in reducing the radioactive enamel abrasion of abrasive materials include the calcium, magnesium or sodium salts selected from the group consisting of the carbonates, bicarbonates, chlorides, phosphates, silicates, and nitrates in amounts of about 0.1 to 5% and preferably 1-5% by weight of the total formulation. In general, calcium is more effective than magnesium which is better than sodium. Similarly, some of the anions are more effective than others as shown in the following table wherein the dentifrice comprising 24% hydrated silicious abrasive and 10% calcined alumina and 5% sodium salt at pH 8 is evaluated.

TABLE IV

| Salt | REA | RDA |
|---|---|---|
| Control | 520 | 340 |
| $NaNO_3$ | 490 | 343 |
| NaCl | 453 | 333 |
| $NaHCO_3$ | 436 | 336 |
| $Na_2HPO_4$ | 395 | 339 |

The magnesium silicate compound found particularly useful has a $MgO:SiO_2$ ratio of 1:2.5 (indicated herein as $Mg-SiO_4$).

Even amounts less than 1% of the additive salt have been found to reduce the abrasivity of an abrasive system comprising hydrated silicious abrasive and calcined alumina. For example, to a composition comprising 20% silicious abrasive and 10% calcined alumina, was added calcium chloride in amounts ranging from 0.1% to 5.0% with the following results in enamel abrasion:

TABLE V

| | Enamel Abrasion REA Value |
|---|---|
| Control (no additive) | 763 |
| 0.1 $CaCl_2$ | 600 |
| 0.3 $CaCl_2$ | 510 |
| 0.5 $CaCl_2$ | 499 |
| 1.0 $CaCl_2$ | 475 |
| 5.0 $CaCl_2$ | 394 |

Amounts in excess of 5% salt additive have been found to have no significant effect in decreasing the abrasivity of the composition below that attained by 5% of said salt as evidenced by the following, wherein sodium bicarbonate was added to a composition comprising 10% calcined alumina and hydrated silicious abrasive with the following results:

TABLE VI

| | % hydrated silicious abrasive | % $NaHCO_3$ | REA | pH |
|---|---|---|---|---|
| (Control) | 24 | 0 | 917 | 7.0 |
| | 24 | 15 | 466 | 8.2 |
| | 20 | 15 | 469 | 8.6 |
| | 24 | 15 | 465 | 8.3 |
| | 24 | 5 | 443 | 8.8 |
| | 24 | 2 | 434 | 8.4 |

These results clearly show that the additive concentration beyond 5% does not beneficially affect enamel abrasion.

Hard, inorganic, mineral-like substances, well known for their abrasive properties, are not generally suitable per se as dentifrice cleaning agents because they are too abrasive. However, the hardness of a certain class of particulate mineral-like substances provide effective cleaning and polishing, while their abrasiveness is minimized by the addition of small amounts of a calcium, magnesium or sodium salt. The addition of an alkaline buffer effects an additional reduction in enamel abrasivity of the dentifrice. The inorganic mineral-like substance should be capable of providing to a dentifrice an REA above about 450 units, when present in an amount of at least about 7.5% by weight of said dentifrice, and should be in particulate form with a mean particle diameter in the range of about 1 micron to 15 microns. The preferred particle size range is 1 to 10 microns. This hard dental abrasive substance is calcined alumina and is capable of providing an REA value above about 450 to a dentifrice. Most commercial dentifrices presently on the market have an REA value up to about 300, and as low as 50.

Calcined alumina is the preferred abrasive in this invention. Flaked calcined alumina is defined as flat flakes of alpha-alumina crystals, of disc- or plate-like configuration, said flakes having a mean (by weight) particle diameter of less than about 7 microns (e.g., about 2 to 7 microns). Viewed under a scanning electron microscope, the flat alumina particles have sharp edges indicating that they have been fractured perpendicular to their flat parallel faces. Generally, the thickness of the flakes are less than about $\frac{1}{2}$ (e.g., about $\frac{1}{8}$ to 1/10) of their diameters, and are in the range of about $\frac{1}{2}$ micron (or less) to about 2 microns (e.g., about 1 micron). The flat alpha-alumina crystals and a process for preparing them are described in U.S. Pat. No. 3,121,623.

Another calcined alumina abrasive useful herein is defined in copending Ser. No. 675,098, filed Apr. 9, 1976, now U.S. Pat. No. 4,060,599, the disclosure of which is incorporated herein by reference, as crystals of alpha-alumina ground to its ultimate particle form and having a mean ultimate particle size of about 1 to 2 microns.

A calcined alumina product available commercially as RC-152 DBM is very dense and highly stable. It has a mean particle size between about 1 to 2 microns, typically about 1.6 microns. Its typical size distribution is as follows:

| Particle Diameter | Percent of Particles Finer than corresponding diameter |
|---|---|
| 10 | about 100 |
| 5 | about 95 |
| 3 | about 85 |
| 2 | about 75 |
| 1 | about 25 |
| 0.5 | about 5 |

Under an electron microscope the larger particles appear flat with sharp sides and the smaller irregularly rounded in circular and oval shapes.

Crystalline alumina RC-152 DBM is ground from a coarser alumina commercially available as RC-152. RC-152 has a crystal particle size such that 98% of the particles pass through a 200 mesh screen and 25% pass through a 100 mesh screen.

The crystalline alpha alumina has been observed to be chemically

| | % by weight | ppm |
|---|---|---|
| $Al_2O_3$ | 99.7 | |
| $Na_2O$ | 0.04 | |
| $SiO_2$ | 0.065 | |
| $Fe_2O_3$ | 0.024 | |
| $TiO_2$ | 0.0016 | |
| MnO | 0.0012 | |
| CaO | 0.045 | |
| $Cr_2O_3$ | 0.00036 | |
| $B_2O_3$ | 0.001 | |
| $F_2$ | | 200 |
| alpha phase alumina | 90 | |

The proportion of the calcined alumina (flat alumina particles) or other hard abrasive in the dentifrice may be, for instance, above 7.5% and in the range of about 7.5 to 20%, preferably about 7.5 to 15%.

In addition to the calcined alumina abrasive, a sufficient amount of silicious abrasive as an additional dental abrasive is preferably included. Accordingly, the silicious abrasive is soft by comparison, and has been conventionally employed in toothpastes. The silicious abrasive particularly useful herein is an amorphous alkali metal or alkaline earth metal alumina-silicate having a refractive index of about 1.44–1.46, and containing at least about 70% silicious abrasive, up to about 10% alumina, up to about 20% by weight of moisture and up to about 10% by weight of sodium oxide, the moisture content preferably being about 10–20% by weight, measured by loss at 1000° C. and the typical content of sodium oxide being about 5–10% by weight. But when little alumina is present in the aluminosilicate, e.g., about 1% or less, the material can be a silica with combined alumina.

The silicious dental abrasive may have a particle size of about 2 to 40 microns and may also be present in the form of relatively large agglomerates (of the individual particles) of such size as to be visible to the naked eye but easily reduced to the fine impalpable particle size upon being subjected to tooth-brushing in the mouth. Such agglomerates may be agglomerated with or without binding agent which may be water-soluble or water-insoluble.

For most purposes it is preferable that the silicious dental abrasive have a particle size less than 20 microns to avoid any gritty feel.

The proportion of this additional silicious dental abrasive in the dentifrice is usually in the range of about 10–70% and preferably 10–50%, and is preferably such that when the alpha alumina is omitted from the dentifrice, the RDA (radioactive dentin abrasion) is in the range of about 100 to 600, and preferably about 100 or 200 to 450.

To make toothpastes or dental creams, the hard abrasive such as the flat flakes of alpha-alumina and the silicious abrasive are dispersed in a dental vehicle which preferably contains a liquid which is water and/or a humectant such as glycerine, sorbitol, xylitol, propylene glycol or polyethylene glycol 400, including suitable mixtures thereof. It is usually advantageous to use a mixture of both water and one or two humectants. Polyethylene glycols of higher molecular weight, e.g., polyethylene glycol 600 etc., may also be present. The total liquid content is generally well over 20% by weight of the vehicle (sorbitol, generally present in admixture with water, is considered as a liquid for this purpose). The preferred humectants are glycerine and sorbitol.

Typically, the vehicle contains about 0–80% by weight of glycerine, up to about 80% by weight of sorbitol and about 5–80% of water.

The calcium, magnesium or sodium salt selected from the group consisting of the carbonates, bicarbonates, chlorides, phosphates, silicates and nitrates, may be added directly to the dental vehicle containing the abrasives, or the abrasives may be pretreated with an aqueous solution of said salt and the pretreated abrasives added to a suitable dental vehicle. The insoluble salts are preferably added directly to the vehicle along with the abrasives because of their water-insolubility. The soluble salts can be dissolved in an aqueous solution and stirred with the abrasives (both the hard and soft abrasive) for five minutes. The solids are then isolated and washed with water. The salt-treated abrasive is then incorporated into a dental vehicle.

The vehicle usually also contains a thickening or gelling agent, such as the natural and synthetic gums and gum-like materials, such as Irish Moss, gum tragacanth, alkali metal (e.g., Li, K or Na) carboxymethyl cellulose and hydroxymethyl carboxyethyl cellulose, polyvinyl pyrrolidone, starch, xylitol, water-soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark Laponite by Laporte Industries, Ltd., and pectin or inorganic thickeners such as colloidal silica, e.g., synthetic finely divided silicas including those sold under the trademarks Cab-O-Sil M5, Syloid 244, Syloid 266, Zeosyl 200 and Aerosil D200. The solid portion of the vehicle is typically present in an amount up to about 10% by weight of the toothpaste and preferably within the range of about 0.5–8% by weight.

Fine particles of thermoplastic resin may also be present, such as particles of solid polymer having a molecular weight above 1000 (and preferably above 10,000, e.g., about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerization or by grinding the polymer in bulk, and may be present in amount of up to about 60% or more of the dentifrice, e.g., in the range of about 20 to 60%, such as about 20 to 50%, e.g., about 30 to 50% in a toothpaste. Examples of thermoplastic resins are polymerized ethylenically unsaturated compounds, such as polyolefines (e.g., polyethylene or polypropylene) or vinyl or vinylidene resins, such as polyvinyl chloride, polystyrene, vinyl chloride-vinyl acetate copolymers, styrene-butadiene copolymers, polyvinylidene chloride; polyamides such as Nylon (e.g., Nylon 6); cellulosics such as cellulose acetate, etc.

The toothpaste may also contain surface-active agents, e.g., to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents are water soluble salts of higher fatty acid monoglyceride monosulfates, such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine, and the sodium, potassium, and ethanolamine salts of N-lauroyl, N-myristoyl or N-palmitoylsarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface active materials include non-ionic agents such as condensates of sorbitan monostearate with approximately 60 moles of ethylene oxide, condensates of ethylene oxide with propylene oxide condensates of propylene glycol ("Pluronics") and cationic surface active germicides and antibacterial compounds such as di-isobutylphenoxyethyldimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure:

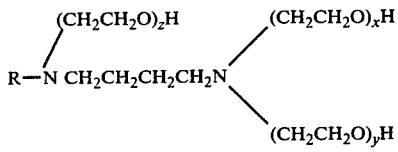

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05–5% by weight, preferably about 1–3%, of the dentifrice.

Various other materials may be incorporated in the oral preparation of this invention. Examples thereof are coloring or whitening agents such as titanium dioxide, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01–5%. Typical examples of such agents are guanidines, biguanides and amines such as:

$N^1$-(4-chlorobenzyl)-$N^5$-2,4-(dichlorobenzyl)biguanide;
p-chlorophenyl biguanide;
4-chlorobenzhydryl biguanide;
4-chlorobenzhydrylguanylurea;
$N^1$-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1, 3-bis (2-ethylhexyl)-5-methylhexahydropyrimidine; and their non-toxic acid addition salts.
Benzethonium chloride
cetyl pyridinium chloride Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, xylitol, sodium cyclamate and saccharin. Suitably, flavor and sweetening agent may together comprise from about 0.01 to 5% or more of the compositions of the instant invention.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thoroughly deaerated (e.g., in vacuo) and tubed.

Preferably the amount of water-insoluble essential flavoring oil is above 0.5% and below 2%. Strongly flavored toothpastes contain above 1% of such flavoring oil, e.g., about 1.2 to 1.5%.

Instant formulations have been found useful as prophylactic dental pastes applied professionally, preparations for use on dentures and for daily use on the teeth.

The following examples are given to illustrate this invention further. In this application all proportions are by weight unless otherwise indicated.

EXAMPLE 1

A toothpaste is prepared according to the following formulation: glycerine 25%; sodium carboxymethyl cellulose 1.4%; sodium benzoate 0.50%; sodium saccharin 0.20%; sodium aluminosilicate (silicious abrasive) 24.0%; titanium dioxide 0.4%; calcined alumina RC-152DBM 10.0%; sodium lauryl sulfate 1.5%; flavoring oil 1.00%; deionized water q.s. This toothpaste has a pH of 7.1 and an REA value of 751.

In changing the pH of this dentifrice by the addition of appropriate acids or bases the following results are obtained:

TABLE VII

|  | pH | REA |
|---|---|---|
| Control | 7.1 | 751 |
|  | 4.5 | 2975 |
|  | 6.0 | 1141 |
|  | 8.1 | 603 |
|  | 9.3 | 506 |

Thus, it is apparent that the pH of the dentifrice has a considerable effect on the abrasivity thereof, with decreased abrasivity being obtained at alkaline pH.

REA represents the radioactive enamel abrasion value obtained by a technique described in the literature.

A method for determining enamel abrasion values for the agents is as follows: Molar teeth are exposed to neutron radiation whereby a predetermined portion of phosphate content is converted to $P^{32}$. Each enamel specimen is mounted in a self- curing polymer such as methyl methacrylate. The specimens are then placed in the specially designed apparatus consisting essentially of a means stabilizing the enamel specimen, a tube to contain the diluted toothpaste and a toothbrush head under a tension of 150 grams. The enamel specimen is then subjected to 4500 reciprocal brush strokes over the cusped surface. A 2.0 ml aliquot is placed in a planchet, dried at room temperature, and the radioactivity ($P^{32}$) determined using a conventional Geiger-Mueller detector. By comparing the radioactivity of the slurries of the experimental pastes to that obtained on each enamel specimen with a reference, calcium pyrophosphate powder which is arbitrarily assigned an enamel abrasion score of 500, the relative abrasiveness of the experimental pastes may be determined.

The RDA values may be suitably determined using the dentin portions separated from human cuspids and subjecting said dentin to 1000 reciprocal brush strokes. This radioactive technique is more fully described in the literature; Stookey, C.K. and Muhler, J.C., J. Dental Research 47 524–538 (1968). Similarly to the REA values, the dentin abrasion must likewise not be high in order to prevent or minimize oral hard tissue damage.

EXAMPLES 2, 3 and 4

Example 1 is repeated except that the silicious abrasive content is reduced to 20% and calcium carbonate is added in amounts of 1%, 3% and 5% while maintaining a pH of 8 with the following results:

|  | % CaCO$_3$ | pH | REA | RDA |
|---|---|---|---|---|
| Example 2 | 1.0 | 8 | 437 | 359 |
| Example 3 | 3.0 | 8 | 395 | 342 |
| Example 4 | 5.0 | 8 | 375 | 371 |

The above results clearly indicate that the addition of a calcium carbonate in an amount as low as 1% and the maintenance of a pH of 8 effects a considerable reduction in the REA value, namely, from 751 of the control to 437. Increasing the amounts of CaCO$_3$ from 1% to 5% effects a greater reduction in enamel abrasivity.

EXAMPLE 5

A sodium alumino-silicate containing 89–91% silica, 0.8–1.2% alumina, 0.3–0.9% sodium oxide and about 10% water is substituted for the silicious abrasive in Example 4; and 8% of a calcined alumina sold under the name "Microgrit" is substituted for the 10% calcined alumina in Example 4. The alpha alumina flakes of the "Microgrit" alumina has a mean particle diameter of about 4 microns, all the particles thereof having diameters less than 10 microns, about 85–95% (by weight) have diameters less than 6.0 microns and about 30–35% have particle diameters less than 3.5 microns. This toothpaste has a pH of 7.8, an REA value of 294 and an RDA value of 461.

EXAMPLE 6

Example 5 is repeated except that the silicious abrasive content is reduced to 20%. The REA value of the dentifrice is 285 and the RDA value is 420. This toothpaste without the 5% CaCO$_3$ has an REA value of 848 and an RDA value of 367.

EXAMPLE 7

Example 1 is repeated except that 5% NaHCO$_3$ is added to the dentifrice. This toothpaste has a pH of 8.4, an REA value of 373, and an RDA value of 409.

EXAMPLE 8

Example 1 is repeated except that the silicious abrasive content is reduced to 20%, the calcined alumina of Example 5 sold as "Microgrit" is substituted for the RC-152 brand, and 5%Mg-SiO$_4$ is added. This toothpaste has a pH of 8.5, an REA value of 377 and an RDA value of 453. This formulation without the MgSiO$_4$ has an REA value of 665 and an RDA value of 394.

EXAMPLE 9

Example 8 is repeated except that the RC-152 brand of calcined alumina is substituted for the "Microgrit". This toothpaste has an REA value of 318 and an RDA value of 464.

EXAMPLE 10

Example 8 is repeated except that 5% CaCO$_3$ is substituted for the 5% Mg-SiO$_4$. This toothpaste has an REA value of 349 and an RDA value of 519.

EXAMPLE 11

Example 8 is repeated except that 5% NaHCO$_3$ is substituted for the 5% Mg-SiO$_4$.
REA = 311, RDA = 490.

EXAMPLES 12a and 12b (a) Example 10 is repeated except that the RC-152 calcined alumina is substituted for the "Microgrit" alumina.
REA = 307, RDA = 498, (b) A calcined alumina having a mean particle diameter of 5 microns (sold as Diamex) is substituted for the "Microgrit". The composition has a pH of 8, REA value of 451 and RDA value of 443.

EXAMPLE 13

Example 1 is repeated except that "Microgrit" alumina is substituted for the RC-152 brand and sodium hydroxide is added until a pH of 9.6 is obtained.
REA = 367.

EXAMPLES 14, 15, 16

Example 1 is repeated except that the silicious content is reduced to 20% and calcium chloride is added in amounts of 1%, 3%, and 5% and the pH is maintained at 8. The following results are obtained:

|  | % CaCl$_2$ | pH | REA | RDA |
|---|---|---|---|---|
| Example 14 | 5.0 | 8 | 319 | 288 |
| Example 15 | 3.0 | 8 | 349 | 294 |
| Example 16 | 1.0 | 8 | 391 | 303 |

The aforementioned results clearly show the reduction in abrasivity effected by the addition of the calcium chloride, with the degree of abrasivity decreasing as the amount of calcium chloride increases from 1 to 5% (control without the calcium chloride has an REA of 751). The drop in REA is greater than that caused by merely raising the pH (REA of 603 at a pH 8 as shown in Example 1). By comparison with insoluble CaCO₃, the soluble CaCl₂ effects a greater REA reduction using the same concentration of salt.

EXAMPLES 17 and 18

Example 1 is repeated except that 1% and 3% MG—SiO₄ is added. Results:

|  | % Mg-SiO₄ | REA |
|---|---|---|
| Example 17 | 1.0 | 588 |
| Example 18 | 3.0 | 526 |

Although the REA is not reduced to the same extent as with the calcium salts, a significant reduction in abrasion is effected, the REA of the control being 751.

EXAMPLE 19

Example 10 is repeated except that the silicous abrasive content is increased to 24%, REA value of 312, and an RDA value of 356. Without the 5% CaCO₃, the REA value of 723 and the RDA value of 430 is obtained. The pH of the resultant composition is 8.0.

EXAMPLE 20

Example 7 is repeated except that 5% CaCO₃ is substituted for the 5% NaHCO₃.
REA = 375, RDA = 353

EXAMPLE 21

Example 11 is repeated except that the RC-152 calcined alumina is used. The resultant toothpaste has a pH of 8.9 and an REA value of 367.

EXAMPLE 22

20% of the sodium alumino-silicate of Example 5 is admixed with 10% "Microgrit" alumina and 5% calcium carbonate. The resultant dentifrice has a pH of 8, an REA value of 367 and an RDA value of 442. The composition without the calcium carbonate has a pH of 6.7, an REA value of 513, and an RDA value of 369.

It is also within the broader scope of the invention to include other alpha aluminas in admixture with the silicious abrasive. An example of another calcined alumina is a pulverized alpha-alumina of irregular shape and having a mean particle size of about 3 to 4 microns (with all said irregular particles being less than about 7 microns in their largest dimension).

Suitable alkaline agents and alkaline buffering agents may be added to further modify the above examples, inclusive of sodium hydroxide, sodium hydrogen phosphate, trisodium phosphate, sodium carbonate-bicarbonate, tetrasodium pyrophosphate and Na₂HPO₄—Na₃PO₄.

While the silicious and calcined alumina abrasives together with the calcium, magnesium or sodium salt has proved most useful thus far in toothpastes, they may also be similarly incorporated into toothpowders or into dental creams which are of pourable consistency.

The particle diameters given in the examples are determined by conventional methods. Thus, the standard liquid sedimentation technique may be used. The calculation of particle diameter from the sedimentation data being made (as is conventional) on the basis of Stokes' Law, disregarding the particular shape of the particles.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A dentifrice toothpaste of superior cleaning and polishing characteristics having a pH maintained above about 7, comprising an alkali metal or alkaline earth metal aluminosilicate as a siliceous abrasive and flat flakes or crystals of alpha alumina as a calcined alumina abrasive having a particle size of about 1 to 15 microns in diameter and in an amount to provide a radioactive enamel abrasion to the dentifrice of above about 450, said calcined alumina being present in an amount of at least 7.5% and up to 20% by weight, and said siliceous abrasive being present in an amount of at least 10% and up to 70% by weight of said dentifrice, and about 0.1 to 5% by weight of a calcium, magnesium or sodium salt, selected from the group consisting of the carbonates, bicarbonates, chlorides, phosphates, silicates and nitrates, so as to reduce said enamel abrasion of the dentifrice.

2. A dentifrice in accordance with claim 1, wherein the pH of the dentifrice is increased by the addition of an alkaline agent to effect an additional reduction in enamel abrasivity.

3. A dentifrice as in claim 2, containing an alkaline buffering agent to maintain a pH above about 7.

4. A dentifrice as in claim 1 in which said calcined alumina is in the form of alpha alumina flakes having a mean particle diameter in the range of 1 to 15 microns.

5. A dentifrice as in claim 1 in which said silicious abrasive is an amorphous alumino-silicate having a particle size of about 2 to 40 microns.

6. A dentifrice as in claim 1, wherein the salt is calcium carbonate and is present in amount of 1-5% by weight and the pH is about 7.8 to 8.0.

7. A dentifrice as in claim 1, wherein the salt is sodium bicarbonate and is present in amount of 1-5% by weight and the pH is about 8.3 to 8.9.

8. A dentifrice as in claim 1, wherein the salt is magnesium silicate and is present in amount of 1-5% by weight and the pH is about 8.1 to 8.5.

9. A dentifrice as in claim 1, wherein the salt is calcium chloride and is present in amount of 1-5% by weight and the pH is about 8.

* * * * *